United States Patent [19]

Kessel et al.

[11] Patent Number: 5,144,051

[45] Date of Patent: Sep. 1, 1992

[54] BRANCHED ALKOXYPHENYL IODONIUM SALT PHOTOINITIATORS

[75] Inventors: Carl R. Kessel; Ellen O. Aeling, both of St. Paul, Minn.

[73] Assignee: Minnesota Mining and Manufacturing Company, St. Paul, Minn.

[21] Appl. No.: 529,639

[22] Filed: May 29, 1990

[51] Int. Cl.$^5$ .................... C07F 13/00; C08G 59/68; C08G 59/72
[52] U.S. Cl. .......................... 556/64; 568/6; 568/13; 522/31; 522/170
[58] Field of Search .................. 556/64; 568/6, 13

[56] References Cited

U.S. PATENT DOCUMENTS

| | | | |
|---|---|---|---|
| 4,279,717 | 7/1981 | Eckberg | 522/31 |
| 4,310,469 | 1/1982 | Crivello | 556/64 |
| 4,882,201 | 11/1989 | Crivello | 522/25 |

Primary Examiner—Marion E. McCamish
Assistant Examiner—Arthur H. Koeckert
Attorney, Agent, or Firm—Gary L. Griswold; Walter N. Kirn; Robert W. Sprague

[57] ABSTRACT

Disclosed are $C_6$ to $C_{11}$ branched chain alkoxy monosubstituted diaryl iodonium salts, such as [4-(2-ethylhexyloxy)phenyl]phenyliodonium hexafluoroantimonate. These diaryl iodonium salts are useful as photoinitiators for epoxy containing compounds, especially epoxysilanes.

2 Claims, No Drawings

BRANCHED ALKOXYPHENYL IODONIUM SALT PHOTOINITIATORS

FIELD OF THE INVENTION

This invention relates to aromatic iodonium salts. Furthermore, this invention relates to photopolymerizable compositions, and more particularly, it relates to such compositions which contain an aromatic iodonium salt as a photoinitiator.

BACKGROUND OF THE INVENTION

Photopolymerizable epoxy compositions containing epoxy resins and various photoinitiators are well known. However, because the existing systems all suffer from one or more drawbacks, there is a continuing need in the industry for improved photoinitiators and photopolymerizable epoxy compositions. Thus, in U.S. Pat. No. 3,074,869, there are disclosed photosensitive epoxy compositions containing a nitrosoamine as a photoinitiator. Compositions of this type require relatively long exposure to a high intensity light source to produce complete polymerization.

In U.S. Pat. Nos. 3,205,157 and 3,708,296, there are disclosed photosensitive epoxy compositions containing aryldiazonium salts of halogen-containing complex anions. Such compositions have limited usefulness because they have poor thermal stability, because their spectral response is limited to the ultraviolet region of the spectrum, and because nitrogen is evolved during photopolymerization causing pinholes and bubbles in heavy coatings of the composition.

When these known aryldiazonium salts are used to induce polymerization of oxetanes, or mixtures of oxetanes with epoxy resins, e.g., as described in U.S. Pat. No. 3,835,003, the same types of problems are encountered. Although several patents describe various techniques for stabilizing mixtures of diazonium salts and epoxides, such techniques are not satisfactory for several reasons. For example, the increase in stability which is obtained is measured only in days. Also, the addition of stabilizers contaminates the compositions with nonreactive material which softens the resulting product and also reduces the rate of photocure. See, e.g., U.S. Pat. Nos. 3,711,390; 3,711,931; 3,816,278; 3,816,280; 3,816,281; and 3,817,845.

Various types of aromatic halonium (typically iodonium or sulfonium) salts have been proposed for use as photoinitiators in photopolymerizable epoxy compositions which do not have the drawbacks associated with nitrosoamine and aromatic diazonium salts.

For example, photopolymerizable epoxy compositions which contain an epoxy-containing material and a photosensitive aromatic iodonium salt are described in U.S. Pat. No. 4,378,277. The aromatic groups of the iodonium salt may be substituted by one or more organic groups including alkoxy groups (e.g., methoxy, ethoxy, butoxy, and the like).

Reference to radiation curable compositions of an epoxy resin and an aromatic halonium salt is made in U.S. Pat. No. 3,968,056 and further discussed in U.S. Pat. No. 4,026,705 where it is disclosed that the aromatic group of the aromatic halonium salt can be substituted with from 1 to 4 monovalent radicals selected from groups including $C_1$ to $C_8$ alkoxy groups. U.S. Pat. No. 4,310,469 also discloses similar radiation curable compositions.

U.S. Pat. No. 4,101,513 discloses polymerizable compositions of a silane and an aromatic onium salt wherein the silane can be a hydrolyzable epoxy-terminated silane and the onium salt can be a diphenyliodonium salt.

U.S. Pat. No. 4,279,717 discloses epoxy functional diorganosiloxane fluids combined with bisaryl iodonium salts, particularly linear alkylate bisdodecylphenyl iodonium salts that will rapidly dissolve in polysiloxane base polymer fluids.

Improvements in the solubilities of aryl iodonium salts in photopolymerizable epoxy compositions, especially epoxypolysiloxanes, are continually sought by the industry. Increased solubility of the particular photosensitive compound in the photopolymerizable polymer solution will, of course, enhance photocuring of the polymer. This improves the performance of the photopolymerized polymer such as, for example, when it is employed as a release coating for a pressure sensitive adhesive.

It was against this background that Applicants sought to develop an improved photoinitiator and photopolymerizable composition.

BRIEF SUMMARY OF THE INVENTION

By this invention, Applicants have discovered that certain types of aromatic iodonium salts have enhanced solubilities in photopolymerizable epoxy compositions and thus, make excellent photoinitiators therefor.

Thus, in one embodiment of the present invention are provided novel aromatic iodonium salts wherein one (and only one) of the aryl groups of the iodonium cation is substituted with one branched chain alkoxy group of 6 to 11 carbon atoms, inclusive. Preferred are branched chain alkoxy groups of 6 to 8 carbon atoms with 8 carbon atoms being most preferred. The anion of the salt is a halogen-containing complex anion.

Provided in another embodiment are photopolymerizable compositions which comprise a compound having an epoxy functionality and an aromatic iodonium salt photoinitiator as defined above.

The novel $C_6$ to $C_{11}$ branched chain alkoxy monosubstituted aromatic iodonium salts of this invention, which have not been specifically disclosed by any of the foregoing cited art, have excellent solubilities in cationically polymerizable epoxy containing compositions. They make excellent photoinitiators and enhance the performance properties of the photocured polymer.

DETAILED DESCRIPTION OF THE INVENTION

The $C_6$ to $C_{11}$ branched chain alkoxy monosubstituted aromatic iodonium salts of the present invention are preferably of the following formula:

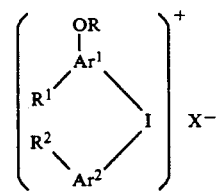

wherein:
Ar$^1$ and Ar$^2$ are independently aromatic groups having from 4 to 20 carbon atoms; preferably Ar$^1$ and Ar$^2$ are independently selected from the group consisting of phenyl, thienyl, furanyl, and pyrazolyl groups; and most preferably Ar¹ and Ar² are both phenyl;

R is a branched chain alkyl group having 6 to 11 carbon atoms; preferably 6 to 8 carbon atoms, and most preferably 8 carbon atoms;

R¹ and R² are hydrogen, alkyl, or together constitute a divalent group (joining Ar¹ and Ar²) selected from the group consisting of

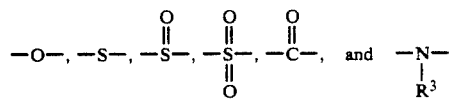

where R³ is hydrogen, an alkyl group of 1 to 6 carbon atoms, a carbon-to-carbon bond, and

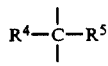

where R⁴ and R⁵ are individually selected from hydrogen, an alkyl group of 1 to 4 carbon atoms, and an alkenyl group of 2 to 4 carbon atoms; preferably R¹ and R² are each hydrogen; and X⁻ is a halogen-containing complex anion, and preferably is selected from the group consisting of tetrafluoroborate, hexafluorophosphate, hexafluoroarsenate, hexachloroantimonate, and hexafluoroantimonate.

Most preferably, the iodonium salts of the present invention are (branched chain octyloxyphenyl)phenyliodonium hexafluoroantimonate having the following structural formula:

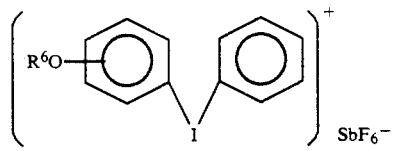

wherein: R⁶ is a branched octyl group such as 2-ethylhexyloxy, 2,4,4-trimethylpentoxy, 2-propylpentoxy or a mixture of such isomers.

Non-limiting examples of the C₆ to C₁₁ branched chain alkoxy monosubstituted aromatic iodonium salts of the invention include:

[4-(isooctyloxy)phenyl]2-pyrazoyliodonium hexafluoroantimonate;
[4-(2-ethylhexyloxy)phenyl]phenyliodonium hexafluoroantimonate;
[4-(2-methylpentoxy)phenyl]phenyliodonium tetrafluoroborate;
[4-(3-methylpentoxy)phenyl]phenyliodonium hexafluorophosphate;
[4-(4-methylpentoxy)phenyl]phenyliodonium hexafluoroantimonate;
[4-(2-propylpentoxy)phenyl]phenyliodonium hexafluoroantimonate;
[4-(2,4,4-trimethylpentoxy)phenyl]phenyliodonium hexafluorophosphate;
[4-(2-ethylheptyloxy)phenyl]phenyliodonium hexafluoroarsenate;
[4-(3,7-dimethyloctyloxy)phenyl]phenyliodonium hexafluoroantimonate;
[4-(2-ethylhexyloxy)phenyl]-2-thienyliodonium hexafluorophosphate; and
[4-(2-ethylhexyloxy)phenyl]2-furanyl-iodonium hexafluoroantimonate.

Aromatic iodonium salts are well known and recognized in the art. See, for example, U.S. Pat. Nos. 3,565,906; 3,712,920; 3,759,989, and 3,763,187; F. Beringer et al., Diaryliodonium Salts IX., J. Am. Chem. Soc. 81, 342-51 (1959); F. Beringer et al., Diaryliodonium Salts XXIII., J. Chem. Soc. 1964, 442-51; and F. Beringer et al., Iodonium Salts Containing Heterocyclic Iodine, J. Org. Chem. 30, 1141-8 (1965).

Aromatic iodonium simple salts may be prepared in accordance with Beringer et al., J. Am. Chem. Soc. 81, 342-51 (1959) by various methods including: (1) coupling of two aromatic compounds with iodyl sulfate in sulfuric acid; (2) coupling of two aromatic compounds with an iodate in acetic acid-acetic anhydride-sulfuric acid; (3) coupling of two aromatic compounds with an iodine acylate in the presence of an acid; and (4) condensation of an iodoso compound, an aromatic iodoso diacetate, or an iodoxyl compound with another aromatic compound in the presence of an acid.

The branched chain alkoxy-substituted iodonium salts of the invention may be prepared as suggested by Beringer's method (4), above, by the condensation of an aromatic iodoso compound, an aromatic iodoso diacetate, or an aromatic iodoxy compound with a branched chain alkoxyaromatic compound in accordance with the following scheme:

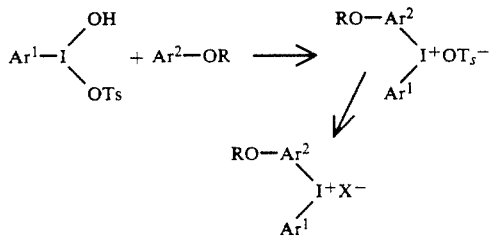

wherein:
Ar¹, Ar², R, and X⁻ are as defined earlier;
Ts is the tosylate group, i.e., p-toluenesulfonyl.

The preferred (branched chain C₆ to C₁₁ alkoxyphenyl)phenyliodonium salts having a halogen-containing complex anion are prepared by a modification of the procedure given by Nieland and Karele, J. Org. Chem. USSR(Eng), 6, 889 (1970) for the preparation of phenyl(p-methoxyphenyl)iodonium tosylate by the condensation of phenyliodoso tosylate with a branched chain C₆ to C₁₁ alkoxybenzene followed by a metathetical exchange of the tosylate anion by a halogen-containing complex anion. Thus, [4-(2-ethylhexyloxy)phenyl]phenyliodonium hexafluoroantimonate can be prepared by contacting at an elevated temperature, e.g., about 50° to 100° C., one equivalent weight of phenyliodoso tosylate and 1.0 to 1.5 equivalent weights of 2-ethylhexyloxybenzene in about 200 parts of a polar aprotic organic solvent, e.g., acetonitrile, for about 1 to 24 hours. The [4-(2-ethylhexyloxy)phenyl]phenyliodonium tosylate obtained does not need to be isolated but can be converted directly to the hexafluoroantimonate by metathesis with an alkali or alkaline earth metal salt of hexafluoroantimonic acid.

Aromatic iodoso tosylates, particularly phenyliodoso tosylate, are well known and are prepared by reaction of an aromatic iodoso acetate with p-toluenesulfonic acid monohydrate. The aromatic iodoso acetates can be prepared, as disclosed by Pausacker, J. Chem. Soc., 1953, 107–9 for the preparation of phenyliodoso acetate, by the reaction of an aromatic iodide and hydrogen peroxide in acetic acid.

Epoxy-containing compositions useful in the present invention are any organic compounds which have an oxirane ring polymerizable by ring opening. Such materials, broadly called epoxides, include monomeric epoxy compounds and epoxides of the polymeric type and can be aliphatic, cycloaliphatic, aromatic, or heterocyclic. These materials generally have at least one polymerizable epoxy group per molecule (preferably two or more epoxy groups per molecule) and in the polymeric type there may be many pendant epoxy groups (e.g., a glycidyl methacrylate polymer could have several thousand pendant epoxy groups per average molecular weight).

These epoxy-containing materials may vary from low molecular weight monomeric materials to high molecular weight polymers and may vary greatly in the nature of their backbone and substituent groups. For example, the backbone may be of any type and substituent groups thereon can be any group not having an active hydrogen atom which is reactive with an oxirane ring. Illustrative of permissible substituent groups include halogens, ester groups, ethers, sulfonate groups, siloxane groups, nitro groups, amide groups, nitrile groups, phosphate groups, etc. The molecular weight of the epoxy-containing materials may run up to 100,000 or more.

Mixtures of various epoxy-containing materials can also be used in the compositions of this invention. Such epoxy-containing materials are well known and include such epoxides as epichlorohydrins, e.g., epichlorohydrin; alkylene oxides, e.g., propylene oxide, styrene oxide, alkenyl oxides, e.g., butadiene oxide; glycidyl esters, e.g., ethyl glycidate; glycidyl-type epoxy resins, e.g., the diglycidyl ethers of Bisphenol A and of novolak resins, such as described in the "Handbook of Epoxy Resins" by Lee and Neville, McGraw-Hill Book Co., New York (1967).

Other useful epoxy-containing materials which can be used in this invention are those which contain one or more cyclohexene oxide groups such as epoxycyclohexanecarboxylates, typified by 3,4-epoxycylcohexylmethyl 3,4-epoxycyclohexanecarboxylate, 3,4-epoxy-2-methylcyclohexylmethyl 3,4-epoxy-2-methylcyclohexanecarboxylate, and bis(3,4-epoxy-6-methylcyclohexylmethyl) adipate. For a more detailed list of useful epoxides of this nature, see, U.S. Pat. No. 3,117,099.

Further epoxy-containing materials which are particularly useful in the practice of this invention include glycidyl ether monomers of the formula:

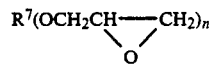

where $R^7$ is alkyl or aryl and n is an integer of 1 to 6. Examples are the glycidyl ethers of polyhydric phenols obtained by reacting a polyhydric phenol with an excess of a chlorohydrin such as epichlorohydrin (e.g., the diglycidyl ether of 2,2-bis(2,3-epoxy propoxyphenol)propane). Further examples of epoxides of this type which can be used in the practice of this invention are described in U.S. Pat. No. 3,018,262.

The epoxypolysiloxanes particularly suitable for use in the compositions of this invention in which the branched chain alkoxy iodonium salts have improved solubility are represented by the formula:

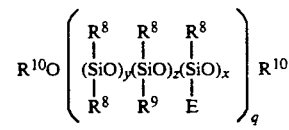

wherein:
$R^8$ is a lower alkyl group of one to three carbon atoms;
$R^9$ is a monovalent hydrocarbyl group of 4 to 20 carbon atoms; and preferably, an alkyl group of 4 to 8 carbon atoms, phenyl, or 2-phenylethyl;
$R^{10}$ is $R_3^8Si—$, $R_2^8ESi—$, or $R_2^8R^9Si—$;
E is an oxiranyl group-substituted monovalent linear, branched, or cyclic aliphatic group having 2 to 300 or more carbon atoms and optionally, up to 100 or more non-peroxidic oxygen atoms; and
q is a number having a value of about 1 to about 75 with the proviso that when x is zero then $R^{10}$ is $R_2^8ESi—$; and
x, y, and z are independently zero or a number having a value up to 200, preferably x is a number having a value between 3 and 50 and y is a number having a value between 33 and 150 such that, when considered with the value of q, the epoxypolysiloxane has a number average molecular weight between 500 and 100,000, preferably between 5,000 and 15,000 and a viscosity of about 100 to 25,000 centistokes.

Illustrative examples of the monovalent organic group $R^8$ in the above formula are alkyl groups such as methyl, ethyl, and propyl. Examples of the monovalent organic groups $R^9$ are butyl, isobutyl, tert-butyl, hexyl, octyl and octadecyl; aryl groups, such as phenyl, tolyl and xylyl; aralkyl groups such as phenylmethyl, phenylethyl, phenylpropyl and phenylhexyl; cycloaliphatic groups such as cyclopentyl, cyclohexyl and 3-cyclohexylpropyl; and ether oxygen- or ester oxygen-containing groups such as ethoxypropyl, butoxybutyl, and ethoxycarbonylpropyl and the like.

The most preferred $R^8$ group is methyl and the most preferred $R^9$ group is phenyl. The siloxane groups in the above formula for the epoxypolysiloxane can be randomly arranged where $R^8$ varies from one group to the next.

The monovalent epoxy group-substituted hydrocarboyl group, E, contains at least one polymerizable epoxy group,

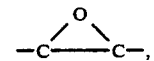

the remainder of the group being composed of carbon and hydrogen and free of acetylenic unsaturation. In addition to the oxirane oxygen, the group can contain ether oxygen, i.e., —O—; carbonyl oxygen, i.e.,

or ester groups, i.e.,

Illustrative examples of E groups are:

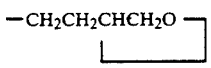

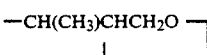

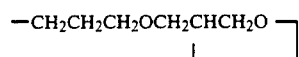

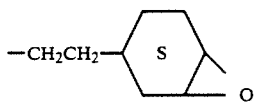

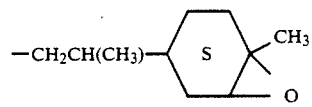

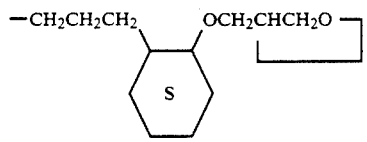

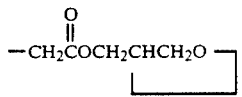

In the above epoxy-containing hydrocarbon groups, the epoxy group is preferably located at the terminal position of the group.

Due to the availability of starting materials and the ease of preparation and performance, the preferred epoxypolysiloxanes are those where $R^8$ is methyl and E is beta-(3,4-epoxycyclohexyl)ethyl or gamma-glycidoxypropyl.

The epoxypolysiloxanes can be prepared by many methods known in the art such as the chloroplatinic acid catalyzed addition reaction of hydrosiloxanes containing the —SiH reactive group with aliphatically unsaturated epoxy compounds; epoxidation of vinyl, alkyl or other unsaturated siloxanes; and Grignard type reactions such as, for example, described by E. P. Pluedemann and G. Fanger, J. Am. Chem. Soc. 81, 2632-35 (1959). A convenient method is the hydrosiloxane addition reaction.

The photopolymerizable compositions of the present invention can be made by admixing the branched chain alkoxy-substituted iodonium salts and other photoinitiator, when used, with the epoxy-containing organic material. The solventless compositions are prepared by dissolving the substituted aromatic iodonium salt and other photoinitiator in the organic material with or without the use of mild heating. The amount of branched chain alkoxy-substituted aromatic iodonium salts employed in the present invention range from about 0.005 to 5 parts, and preferably about 0.5 to 2.0 parts, per 100 parts of cationically polymerizable material.

The branched chain alkoxy-substituted aromatic iodonium complex salts useful in the compositions of the invention are of themselves photosensitive to radiation only in the ultraviolet range of the spectrum. They, however, can be sensitized to radiation in the near ultraviolet and the visible range of the spectrum by sensitizers for known photolyzable organic halogen compounds in accordance with the teachings of U.S. Pat. No. 3,729,313. Illustrative sensitizers are found in the following categories: aromatic amines and colored aromatic polycyclic hydrocarbons. The use of strongly basic amino compounds is less desirable.

Wavelengths of radiation to which the polymerizable compositions of the invention are sensitive are in the 200 to 600 nm range, preferably 200 to 450 nm. Suitable sources include sunlight, carbon arcs, mercury vapor arcs, black light lamps, fluorescent lamps, argon and xenon glow lamps, electronic flash units and flood lamps. Depending on the concentration of the iodonium salt, the particular epoxypolysiloxane, and the depth of the composition, exposures necessary to polymerize (which term includes crosslink and cure) the composition range from about 1 second or less to about 10 minutes or longer. Where the activating radiation is above about 300 nm, it is desirable to include in the photosensitive radiation sensitizer such as 1,3-diphenylisobenzofuran, 2-isopropyl thioxanthone or 1,3-diphenyl-2-pyrazoline. Other useful sensitizers are disclosed in U.S. Pat. No. 4,250,053.

The polymerization of the composition of the invention is a triggered reaction, i.e., once the degradation of the aromatic iodonium complex salt has been initiated by exposure to a radiation source, the hardening reaction proceeds and will continue after the radiation source is removed. The use of thermal energy during or after exposure to a radiation source will generally accelerate the hardening reaction and even a moderate increase in temperature may greatly accelerate the hardening rate.

Substrates which may be coated with the polymerizable compositions of the present invention include substrates of wood, fiberboard, particle board, paper and cardboard; synthetic and natural polymers such as polyolefins, polyesters, cellulose esters, polyamides, cured phenolics, urea-formaldehyde resins, poly(vinyl halides), polyacrylates, polyurethanes, proteins, and rubber; inorganic substrates such as iron, stainless steel, copper, brass, bronze, aluminum, titanium, nickel, zinc, and alloys. Particularly useful substrates are paper, silicated aluminum, polypropylene, poly(vinyl)chloride, the polyesters such as polyethylene terephthalate, and cellulose esters such as cellulose acetate.

The solventless actinic radiation polymerizable compositions of the invention are particularly suitable for preparing release liners for use with adhesive roll and sheet materials. For this use, a substrate of paper or a film of polymers such as, for example, polyester, polyamide, polyolefin, etc., is used. Where needed, primers such as 2-(3,4-epoxycyclohexyl)ethyltrimethoxysilane may be used to improve adherence of the radiation-cured composition to the substrate without effecting the release performance of the epoxypolysiloxane coating.

In the examples given later herein, evaluation of release coatings prepared using the aromatic iodonium salts of the present invention was done by the following tests:

RELEASE VALUE

A standard pressure-sensitive adhesive tape having an acrylic pressure-sensitive adhesive, i.e., a 95.5:4.5 isooctyl acrylate:acrylic acid copolymer, as described in U.S. Pat. No. Re. 24,906, was pressed against the surface of a release coated substrate using two passes of a 2 kg rubber roller to produce a laminate. The laminate was cut into 2.5×25 cm strips and attached, substrate side down, to a smooth stainless steel panel. The release value is the force, in grams, required to pull the pressure-sensitive adhesive tape with adhesive adhered thereto away from the release coated substrate at an angle of 180° and a pulling speed of 30 cm/min.

HEAT AGED RELEASE VALUE

A laminate of standard pressure-sensitive adhesive tape and release coated substrate was prepared as described above and heated in an oven at 70° C. for 20 hours. After this time, the laminate was removed from the oven, allowed to cool for at least 10 minutes in a room at 23°+0.2° C. and 50+2% R.H. and within 2 hours after removal from the oven, the force required to pull the pressure sensitive tape with adhesive adhered thereto away from the release coated substrate was measured as described in the above test.

READHESION TEST

The pressure-sensitive tape, as removed from the release-coated substrate, was pressed to the surface of a clean glass plate using two passes of a 2 kg rubber roller. The readhesion efficiency is the quotient of the force, in grams, required to pull the tape from the glass surface at an angle of 180° and stripping speed of 30 cm/sec divided by the force in grams required to pull a virgin tape that has not been contacted with a release-coated substrate from the glass plate times one hundred (expressed as a percentage).

The present invention is further illustrated by the following examples, but the particular materials and amounts thereof recited in these examples, as well as other conditions and details, should not be construed to unduly limit this invention. In the following examples, unless indicated otherwise, parts and percentages are parts and percentages by weight and temperatures are in degrees centigrade.

EXAMPLE 1

A solution of 218 parts of 2-ethylhexyl phenyl ether in 450 parts acetonitrile was heated to 70° C., and 457 parts phenyl iodosotosylate (prepared according to Koser et al., *J. Org. Chem.* 1980, 45, 1543) was added in one portion. The solution was stirred at 70° C. for 6 hours, allowed to cool, and filtered. The filtrate was stirred over 50 parts of NaNHCO$_3$, refiltered, and concentrated under reduced pressure to about one-half the original volume. A suspension of 274 parts of sodium hexafluoroantimonate in 720 parts ethyl acetate was slowly added to the concentrated solution, causing a large volume of precipitate to form. This suspension was allowed to stir at room temperature for 30 minutes, filtered, and all solvent was removed under reduced pressure followed by high vacuum to give 716 parts of an orange syrup. The NMR and IR spectra of this product confirm that it is a mixture of products of which about 85% by weight is the desired [4-(2-ethylhexoxy)-phenyl]phenyliodonium hexafluoroantimonate.

EXAMPLES 2-5

Additional branched-chain alkoxyiodonium hexafluoroantimonate salts were prepared in a manner similar to that given for Example 1. In some cases, a slight excess of sodium hexafluoroantimonate was used to ensure complete conversion of the initially formed iodonium tosylate to the hexafluoroantimonate anion. Residual sodium hexafluoroantimonate would affect the apparent solubility behavior of the materials, so all of the Examples 1-5 (as well as the following comparative Examples 6-9) were dissolved in an equal volume of dichloromethane, filtered, and stripped to remove any inorganic salts.

Table 1 lists the branched chain alkoxyiodonium salts which have been prepared as examples of this invention. The physical state of the materials as prepared is included as an indication of the relative crystallinity of the iodonium salts. These products were not highly purified, but they were prepared under similar conditions, and the physical state as shown in Table 1 (and Table 2) should be viewed as an indication of the relative tendency of these materials to solidify.

TABLE 1

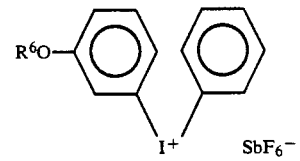

| Example | R$^6$ | | Physical State |
|---|---|---|---|
| 1 | 2-ethylhexyl | (i-C$_8$) | syrup |
| 2 | iso-octyl | (i-C$_8$') | syrup |
| 3 | 2-ethyl-1-butyl | (i-C$_6$) | syrup |
| 4 | 3,7-dimethyl-1-octyl | (i-C$_{10}$) | waxy solid |
| 5 | 2,4-diethyl-1-heptyl | (i-C$_{11}$) | waxy solid |

Straight-chain alkoxyiodonium hexafluoroantimonate salts were prepared in a manner identical to the materials prepared in Examples 1-5. These materials, prepared for comparison with the branched chain alkoxy aromatic iodonium salts of this invention, were synthesized in the same manner as outlined in Example 1. Table 2 lists these materials along with the physical state as discussed above.

TABLE 2

| Example | R$^6$ | Physical State |
|---|---|---|
| 6 | n-octyl (n-C$_8$) | waxy solid |
| 7 | n-hexyl (n-C$_6$) | solid |
| 8 | n-decyl (n-C$_{10}$) | solid |
| 9 | n-undecyl (n-C$_{11}$) | solid |

EXAMPLE 10

The solubility and effectiveness of each iodonium salt in an epoxypolysiloxane of the formula:

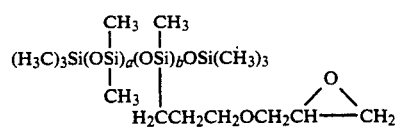

where a=63 and b=7 (on average) and having an epoxy equivalent weight (EEW) of 865 was determined by mixing 2% by weight of the aromatic iodonium salt into the epoxypolysiloxane with vigorous stirring. Each sample was then allowed to sit for several days, vigorously restirred, and allowed to sit undisturbed in the dark for one week in order to allow any insoluble material to settle to the bottom. Photospeed of the resulting formulations was checked by withdrawing a sample from the top of the container, coating onto biaxially oriented polypropylene film using a blade coater, and exposing to UV light in an RPC UV processor with two medium pressure mercury lamps running at 300 watts/inch. The maximum speed (in feet per minute) at which a coating could be passed through the UV processor while still obtaining cure is designated as $V_{max}$. Cure of the coatings was judged by wiping the coatings with light finger pressure 10 seconds after exiting the UV processor; a coating which did not mar under these circumstances was judged to be cured. Coating weights of all of the materials were approximately 1 gram/square meter of film.

TABLE 3

| Example | Iodonium | $V_{max}$ (fpm) |
|---|---|---|
| 1 | i-$C_8$ | 100 |
| 2 | i-$C_8$ | 100 |
| 3 | i-$C_6$ | 100 |
| 4 | i-$C_{10}$ | <50 |
| 5 | i-$C_{11}$ | 50 |
| 6 | n-$C_8$ | <50 |
| 7 | n-$C_6$ | 50 |
| 8 | n-$C_{10}$ | <50 |
| 9 | n-$C_{11}$ | 50 |

The foregoing data show that the inventive branched chain $C_6$ to $C_{11}$ alkoxy group substituted aromatic iodonium salts give results which are at least equal to, and in some instances (i-$C_6$ and i-$C_8$) superior to, the non-inventive aromatic iodonium salts when employed as photoinitiators in epoxypolysiloxanes.

EXAMPLE 11

The solubility and effectiveness of each iodonium salt in an epoxypolysiloxane having the formula:

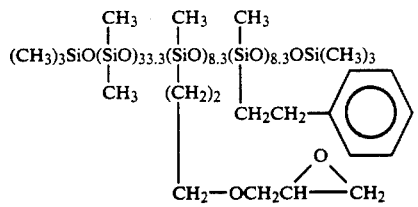

and having an epoxy equivalent weight of 647, was determined in a manner identical to that described in Example 10. The results of these tests are presented in Table 4.

TABLE 4

| Example | Iodonium | $V_{max}$ (fpm) |
|---|---|---|
| 1 | i-$C_8$ | 300 |
| 2 | i-$C_8'$ | 300 |
| 3 | i-$C_6$ | 300 |
| 4 | i-$C_{10}$ | 200 |
| 5 | i-$C_{11}$ | 200 |
| 6 | n-$C_8$ | 200 |
| 7 | n-$C_6$ | 200 |
| 8 | n-$C_{10}$ | <50 |

TABLE 4-continued

| Example | Iodonium | $V_{max}$ (fpm) |
|---|---|---|
| 9 | n-$C_{11}$ | 50 |

The above data show that the branched chain alkoxy substituted aromatic iodonium salts out performed their respective straight chain counterparts in all instances when employed in epoxypolysiloxanes.

EXAMPLE 12

The solubility and effectiveness of each iodonium salt in an epoxypolysiloxane of the same formula as the epoxypolysiloxane that was used in Example 10, but where a=54.4 and b=15.6 (on average) and having an epoxy equivalent weight of 445, was determined in a manner identical to that described in Example 10. The results of these tests are presented in Table 5.

TABLE 5

| Example | Iodonium | $V_{max}$ (fpm) |
|---|---|---|
| 1 | i-$C_8$ | 400 |
| 2 | i-$C_8$ | 400 |
| 3 | i-$C_6$ | 200 |
| 5 | i-$C_{11}$ | 200 |
| 6 | n-$C_8$ | 400 |
| 7 | n-$C_6$ | 150 |
| 8 | n-$C_{11}$ | <50 |

The above data show that the branched chain alkoxy substituted aromatic iodonium salts of this invention were at least equal to, and in several instances were superior to the performance of their straight chain counterparts when employed in epoxypolysiloxanes.

EXAMPLE 13

This example illustrates the utility of a cured photopolymerizable composition of the present invention as a release coating for an adhesive.

A coating composition was prepared by mixing 98 parts of an epoxypolysiloxane having the same formula as the epoxysiloxane that was used in Example 10 with 2 parts of the 2-ethylhexoxy substituted iodonium salt of Example 1 and 0.1 parts of 2-isopropyl thioxanthone. A 0.5 to 1.0 micron thick layer of this clear yellow solution was coated onto a 50 micron thick biaxially oriented polypropylene film using a 3 roll offset gravure coater. The coated film was then passed under four medium pressure mercury lamps to give a clear, non-tacky, non-smearing composite film.

The release properties of this coated film to an acrylic adhesive were evaluated as described above. Both initial and heated aged release values were approximately 10 grams/2.5 cm width with readhesion efficiencies of greater than 95%.

Reasonable modifications and variations are possible from the foregoing disclosure without departing from either the spirit or scope of the present invention.

We claim:

1. An aromatic iodonium salt represented by the formula:

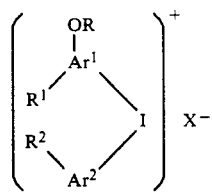

wherein:
Ar$^1$ and Ar$^2$ are phenyl;
R is a branched chain alkyl group having 6 to 8 carbon atoms;
R$^1$ and R$^2$ are hydrogen; and
X$^-$ is a halogen-containing complex anion selected from the group consisting of: tetrafluoroborate, hexafluorophosphate, hexafluoroarsenate, hexachloroantimonate, and hexafluoroantimonate.

2. An aromatic iodonium salt according to claim 1 wherein:
R$^1$ is 2-ethylhexyl; and
X$^-$ is hexafluoroantimonate.

* * * * *